(12) United States Patent
Chu

(10) Patent No.: US 9,926,565 B2
(45) Date of Patent: Mar. 27, 2018

(54) APTAMER-RNAI THERAPEUTIC COMPOSITIONS

(71) Applicants: OREGON HEALTH & SCIENCE UNIVERSITY, Portland, OR (US); THE UNITED STATES OF AMERICA AS REPRESENTED BY THE DEPARTMENT OF VETERANS AFFAIRS, Washington, DC (US)

(72) Inventor: Cong-Qiu Chu, Lake Oswego, OR (US)

( * ) Notice: Subject to any disclaimer, the term of this patent is extended or adjusted under 35 U.S.C. 154(b) by 0 days.

(21) Appl. No.: 14/862,065

(22) Filed: Sep. 22, 2015

(65) Prior Publication Data

US 2016/0083731 A1   Mar. 24, 2016

Related U.S. Application Data

(60) Provisional application No. 62/054,135, filed on Sep. 23, 2014.

(51) Int. Cl.
*A61K 9/00* (2006.01)
*C12N 15/115* (2010.01)
*A61K 31/7088* (2006.01)
*C12N 15/113* (2010.01)

(52) U.S. Cl.
CPC ........ *C12N 15/115* (2013.01); *A61K 31/7088* (2013.01); *C12N 15/1138* (2013.01); *C12N 2310/14* (2013.01); *C12N 2310/16* (2013.01); *C12N 2310/3519* (2013.01); *C12N 2310/531* (2013.01)

(58) Field of Classification Search
USPC .... 435/6.1, 91.1, 91.31, 320.1, 455; 514/44; 536/23.1, 24.5
See application file for complete search history.

(56) References Cited

PUBLICATIONS

Song et al, Biochem. Biophys. Res. Commun., vol. 452, No. 4, pp. 1040-1045 (published online Sep. 18, 2014).*
U.S. Appl. No. 15/600,575.*
Bouchard, et al., "Discovery and development of therapeutic aptamers," Annu. Rev. Pharmacol. Toxicol., vol. 50, 2010, pp. 237-257.
Burgler, et al., "RORC2 Is Involved in T Cell Polarization through Interaction with the FOXP3 Promoter," J. Immunol., vol. 184, 2010, pp. 6161-6169.
Garber, et al., "Anti-IL-17 mAbs herald new options in psoriasis," Nat. Biotechnol., vol. 30, No. 6, 2012, pp. 475-477.
McNamara, et al., "Cell type-specific delivery of siRNAs with aptamer-siRNA chimeras," Nat. Biotechnol., vol. 24, 2006, pp. 1005-1015.
Neff, et al., "An aptamer-siRNA chimera suppresses HIV-1 viral loads and protects from helper CD4(+) T cell decline in humanized mice," Science Transl. Med., vol. 3, No. 66, 2011, 20 pages.
Song, et al., "CD4 aptamer-RORgammat shRNA Chimera Inhibits IL-17 Synthesis by Human CD4+ T cells," Biochem Biophys. Res Commun., vol. 452, No. 4, 2014, pp. 1040?-1045.
Search Report dated Dec. 31, 2015 in International Application No. PCT/US2015/051553.

* cited by examiner

*Primary Examiner* — Jane Zara
(74) *Attorney, Agent, or Firm* — Ballard Spahr LLP

(57) ABSTRACT

A recombinant nucleic acid comprising an aptamer that binds CD4 and an RNAi sequence that silences the expression of RORγ2 is described herein. Pharmaceutical compositions comprising the recombinant nucleic acid, particularly topical compositions are also described. Methods of treating inflammatory disease using the pharmaceutical composition are also described.

12 Claims, 14 Drawing Sheets

APTAMER-RNAI THERAPEUTIC COMPOSITIONS

FIELD

Generally, the field is nucleic acid compositions used in the treatment of disease. More specifically, the field is nucleic acid compositions comprising an aptamer that binds CD4 fused to an RNAi molecule that silences RORγt.

BACKGROUND

RNA interfering (RNAi)-mediated gene silencing holds great promise for manipulating T cells to study basic T cell biology and for developing potential T cell targeted therapeutics.

Many autoimmune and/or inflammatory diseases are mediated by Th17 cells. These include rheumatoid arthritis, multiple sclerosis, systemic lupus erythematosus, psoriasis, inflammatory bowel disease, and type 1 diabetes mellitus (Rao D D et al, *Adv Drug Deliv Rev* 61, 746-759 (2009); incorporated by reference herein).

The retinoic acid receptor related orphan receptor gamma 2 gene encodes RORγt. RORγt is required for the differentiation of Th17 cells. Th17 cells produce several inflammatory cytokines, including IL-17, IL-17F, IL-22 and IL-21 which all have been implicated in mediating the chronic inflammation that is characteristic of a number of autoimmune inflammatory diseases.

New therapeutics that specifically target Th17 cells rather than targeting members of the IL-17 family or ubiquitous IL-17 receptors are needed.

SUMMARY

Disclosed herein are recombinant polyribonucleotides comprising a first sequence that includes an aptamer that specifically binds CD4 and a second sequence that includes an RNAi that silences RORγt. The polynucleotide can be chemically synthesized or transcribed from a DNA template (including in vitro transcribed.) In some examples, the polyribonucleotide includes a CD4-specific aptamer sequence encoded by SEQ ID NO: 5. In other examples, the polyribonucleotide includes a RORγt specific RNAi sequence encoded by SEQ ID NO: 7. The polyribonucleotide can include a 2'-fluroribonucleic acid. One example of the recombinant polyribonucleotide is a polyribonucleotide that includes SEQ ID NO: 1.

Disclosed herein are expression vectors comprising the recombinant polyribonucleotides described herein operably linked to a promoter. In some examples, the expression vector is stably transfected in a cell.

Disclosed herein are pharmaceutical compositions comprising an effective amount of the recombinant polyribonucleotides described herein, including pharmaceutical compositions formulated for topical administration.

Disclosed herein are methods of treating diseases mediated by Th17 cells in subject. Those methods include administering the pharmaceutical compositions described herein to the subject. Such diseases include arthritis, multiple sclerosis, systemic lupus erythematosus, psoriasis, inflammatory bowel disease, and type 1 diabetes mellitus.

Disclosed herein are pharmaceutical compositions for use in treating diseases mediated by Th17 cells in a subject.

AshR-RORγt chimera; Blue line, Mock-CD4-AshR-RORγt chimera (representative of three experiments). The x-axis indicates RORγt expression with higher expression on the right.

Figure 3A:
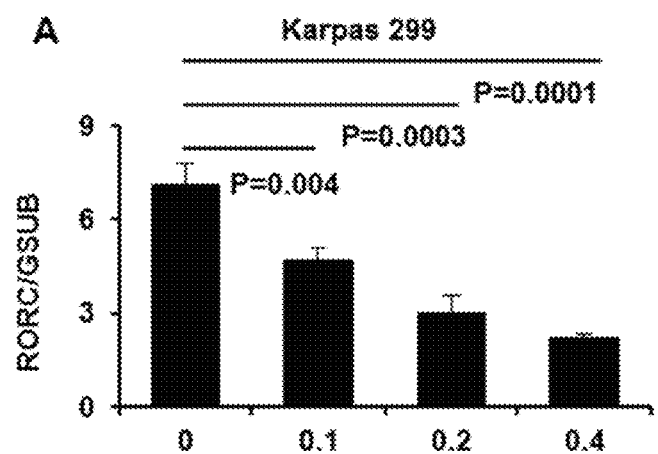
FIG. 3A is a bar graph depicting the results of a quantitative real-time PCR assay for RORγt gene expression. RORγt gene expression was significantly reduced by CD4-AshR-RORγt chimera in a concentration-dependent manner in Karpas 299 cells.
Figure 3B:
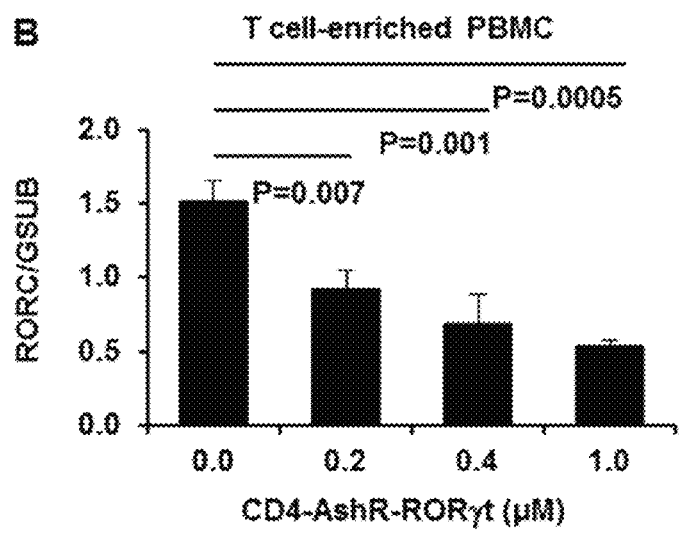
FIG. 3B is a bar graph depicting the results of a quantitative real-time PCR assay for RORγt gene expression in T-cell enriched PBMCs Mock-CD4-AshR-RORγt chimera, CD4-AshR-scrambled control or CD4-AshR-CCR5 chimera had no effect on RORγt gene expression in T-cell enriched PBMCs.
Figure 3C:
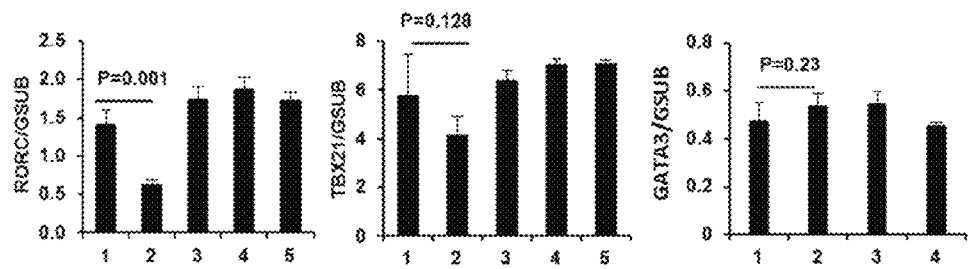
FIG. 3C is a set of three bar graphs showing that all the chimeras lacked a significant inhibition on TBX21 or GATA3 in T-cell enriched PBMCs. (Data are presented as mean±SD of three experiments). 1, PBS; 2, CD4-AshR-RORγt chimera; 3, mock-CD4-AshR-RORγt chimera; 4, CD4-AshR-scrambled control chimera; 5, CD4-AshR-CCR5 chimera.
Figure 3D:
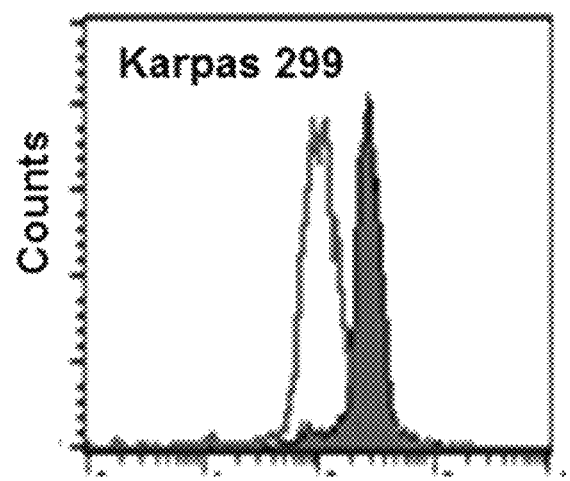
FIG. 3D is a FACS plot showing RORγt protein expression analyzed by flow cytometry in Karpas 299 cells were stimulated with PMA 50 ng/ml for 24 h. Red line, CD4-
Figure 3E:
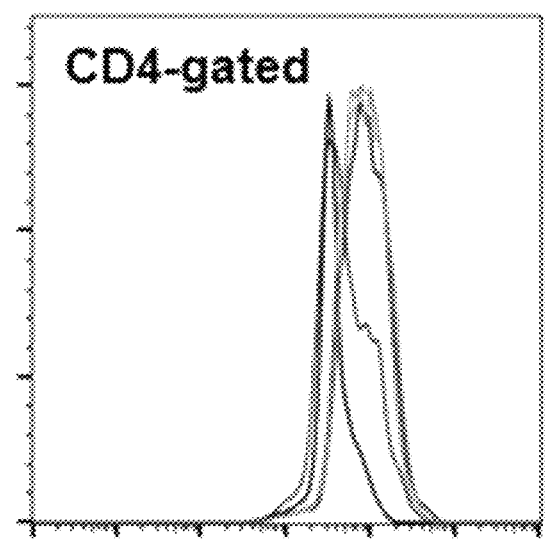

FIG. 3E is a FACS plot showing RORγt protein expression in PBMCs stimulated with anti-CD3/CD28 and LPS for 48 h. RORγt expression was reduced by CD4-AshR-RORγt chimera (red line), but not by mock-CD4-AshR-RORγt chimeras (blue line) or CD4-AshR-scrambled control chimera (purple line). Black line, PBMCs without stimulation; green line, PBMCs with stimulation but without chimeras (representative of three experiments). The x-axis indicates RORγt expression with higher expression on the right.

Figure 3F:
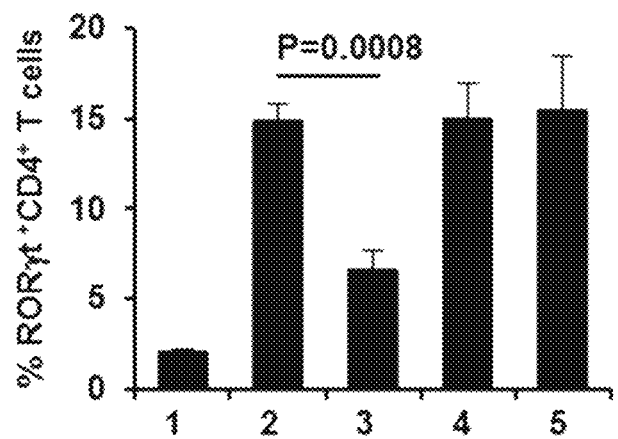

FIG. 3F is a bar graph showing the percentage of RORγt+ cells in stimulated T-cell enriched PBMCs was reduced by CD4-AshR-RORγt, but not by mock-CD4-AshR-RORγt chimera or CD4-AshR-scrambled control chimera. 1, PBMCs without stimulation; 2, PBMCs with stimulation but without chimeras; 3, Stimulated PBMCs were treated with CD4-AshR-RORγt chimeras; 4, Stimulated PBMCs were treated with mock-CD4-AshR-RORγt chimera; 5, Stimulated PBMCs were treated with CD4-AshR-scrambled control chimera (Data are presented as mean±SD of three experiments).

Figure 4A:
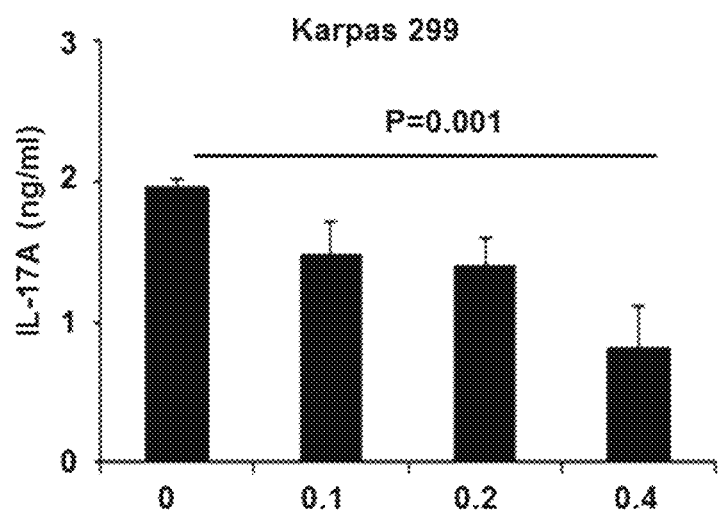

FIG. 4A is a bar graph showing expression of IL-17A in the supernatant of Karpas 299 cells stimulated with PMA measured by ELISA. X-axis shows concentration of added CD4-AshR-RORγt.

Figure 4B:
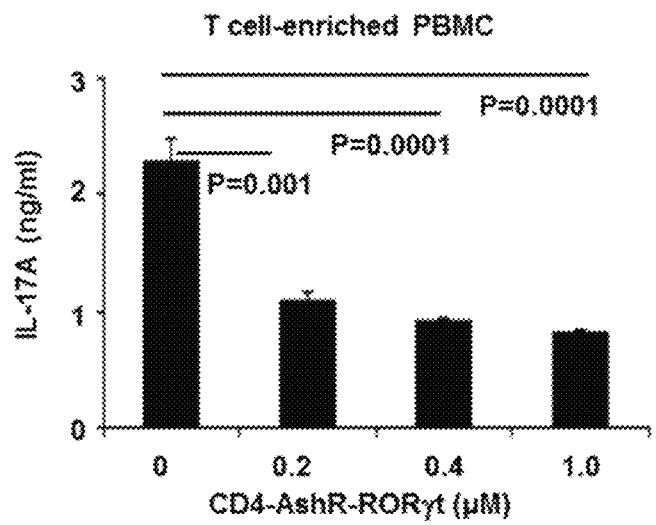

FIG. 4B is a bar graph showing expression of IL-17A in the supernatant of T cell enriched PBMC stimulated with anti-CD3/CD28 measured by ELISA. X-axis shows concentration of CD4-AshR-RORγt.

Figure 4C:
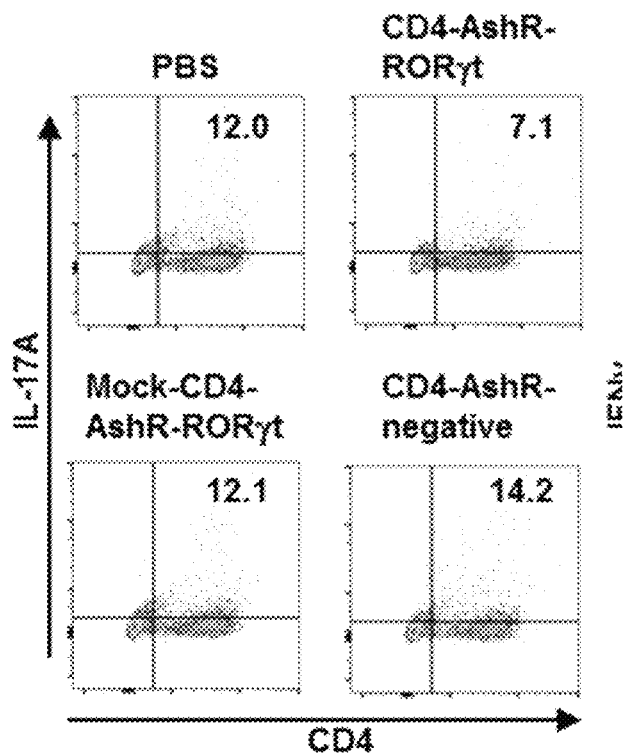

FIG. 4C is a FACS plot showing fewer IL-17A producing CD4+ T cells in the presence of CD4-AshR-RORγt chimera relative to negative controls.

Figure 4D:
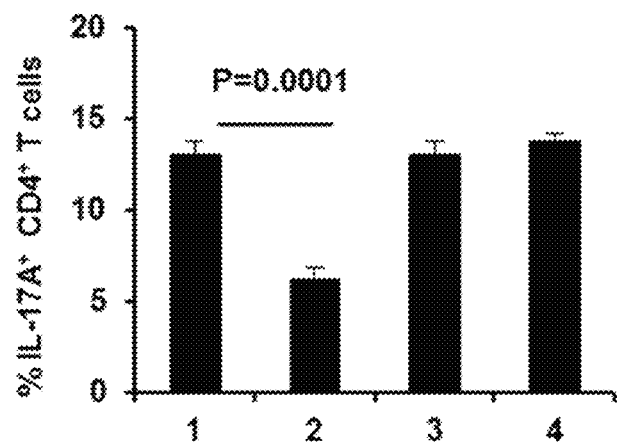

FIG. 4D is a bar graph recapitulating the data from FIG. 4C. 1, PBS; 2; CD4-AshR-RORγt chimera; 3, mock-CD4-AshR-RORγt chimera; 4, CD4-AshR-scrambled control chimera (Data are presented as mean±SD of three experiments).

Figure 4E:
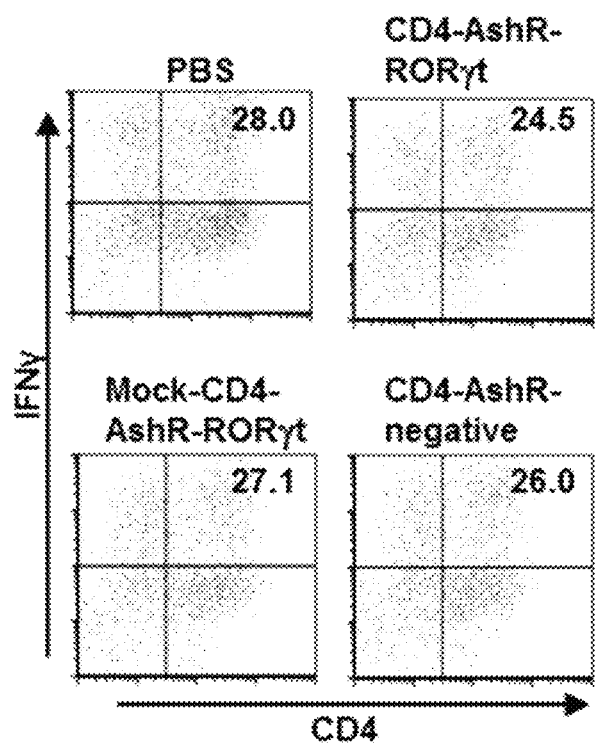

FIG. 4E is a FACS plot showing no effect of IFN-γ producing CD4+ T cells in PBMC in the presence of CD4-AshR-RORγt chimera relative to negative controls.

Figure 4F:
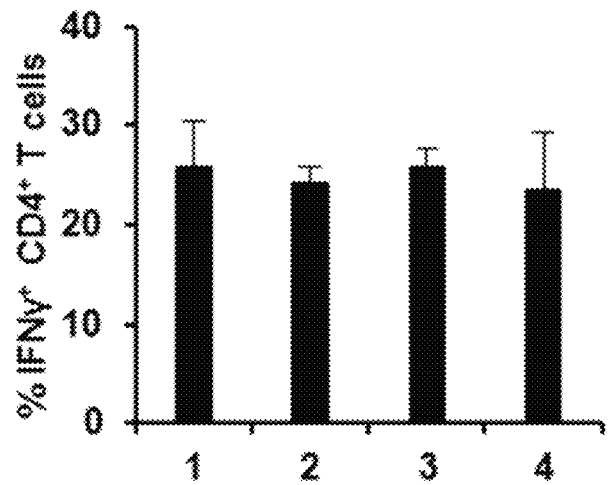

FIG. 4F is a bar graph recapitulating the data from FIG. 4E. 1, PBS; 2; CD4-AshR-RORγt chimera; 3, mock-CD4-AshR-RORγt chimera; 4, CD4-AshR-scrambled control chimera.

Figure 4G:
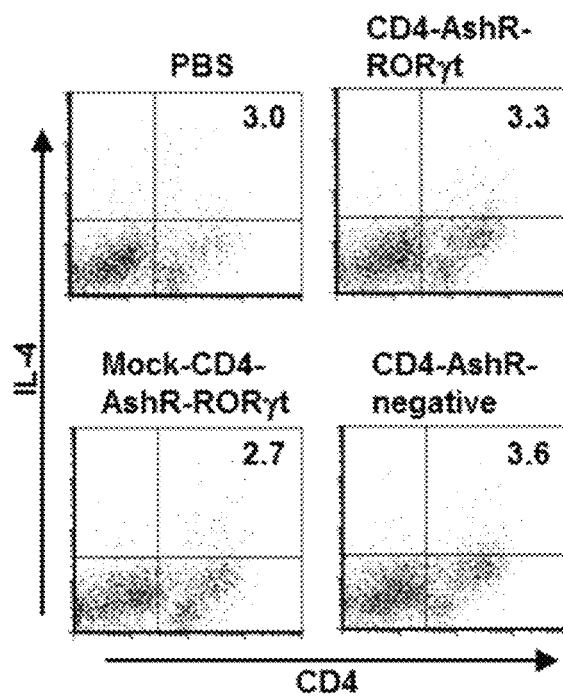

FIG. 4G is a FACS plot showing no effect of IL-4 producing CD4+ T cells in PBMC in the presence of CD4-AshR-RORγt chimera relative to negative controls.

Figure 4H:
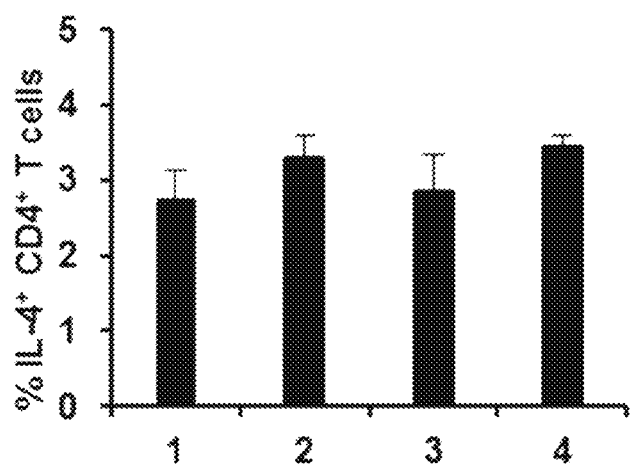

FIG. 4H is a bar graph recapitulating the data from FIG. 4E. 1, PBS; 2; CD4-AshR-RORγt chimera; 3, mock-CD4-AshR-RORγt chimera; 4, CD4-AshR-scrambled control chimera.

SEQUENCE LISTING

SEQ ID NO: 1 is a CD4-aptamer RORγt shRNA chimera.
SEQ ID NO: 2 is a negative control chimera that includes a mock CD4 binding aptamer and an intact RORγt shRNA.
SEQ ID NO: 3 is a negative control chimera that includes an intact CD4 binding aptamer and a scrambled shRNA
SEQ ID NO: 4 is a negative control chimera that includes an intact CD4 binding aptamer and a CCR5 shRNA.
SEQ ID NO: 5 is a DNA sequence encoding a CD4 binding aptamer.
SEQ ID NO: 6 is a DNA sequence encoding a negative control aptamer
SEQ ID NO: 7 is a DNA sequence encoding a RORγt shRNA.
SEQ ID NO: 8 is a DNA sequence encoding a scrambled shRNA.
SEQ ID NO: 9 is a DNA sequence encoding a CCR5 shRNA.

DETAILED DESCRIPTION

Terms:
Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCR Publishers, Inc., 1995 (ISBN 1-56081-569-8).

In order to facilitate review of the various embodiments of the disclosure, the following explanations of specific terms are provided:

Administration: To provide or give a subject an agent, such as a therapeutic agent, by any effective route. Exemplary routes of administration include, but are not limited to, injection (such as subcutaneous, intramuscular, intradermal, intraperitoneal, and intravenous), oral, intraductal, sublingual, rectal, transdermal, topical, intranasal, vaginal and inhalation routes.

Aptamer: An oligonucleotide of a single defined sequence that binds specifically to a target molecule. An aptamer can be single- or double-stranded. In some examples an aptamer is conjugated to an RNAi and can thereby deliver the RNAi to a cell expressing a target molecule (such as a protein) to which the aptamer can specifically bind. Aptamers can range between 10 and 100 nucleotides in length, including 15 to 40 nucleotides or 20 to 40 nucleotides.

Binding or stable binding: An association between two substances or molecules, such as the association of an aptamer with a protein or other target molecule. Binding can be detected by any procedure known to one skilled in the art, such as by physical or functional properties. Binding can be determined by binding a labeled version of an aptamer to the target molecule, then detecting the presence of the target on cells also known to express the target molecule using, for example, two color flow cytometry. Binding can be detected functionally by determining whether binding has an observable effect upon a biosynthetic process such as expression of a gene (including RNAi mediated silencing), DNA replication, transcription, translation, protein activity and the like.

Contacting: Placement in direct physical association, including contacting of a solid with a solid, a liquid with a liquid, a liquid with a solid, or either a liquid or a solid with a cell or tissue, whether in vitro or in vivo. Contacting can occur in vitro with isolated cells or tissue or in vivo by administering to a subject.

CD4: (Cluster of differentiation 4) is a glycoprotein found on the surface of various cells of the immune system. CD4 is expressed most predominantly on helper T cells (Th) cells, but it may also be expressed by antigen presenting cells such as macrophages and dendritic cells.

Effective amount: An amount of agent, such as a polyribonucleotide comprising SEQ ID NO: 1 that is sufficient to generate a desired response, such as the reduction or elimination of a sign or symptom of a condition or disease, such as a Th17 mediated disease. Alternatively, an effective amount may be an amount sufficient to generate a desired response in an animal model of a Th17 mediated disease.

When administered to a subject, a dosage will generally be used that will achieve target tissue concentrations that have been shown to achieve activity in vitro. In some examples, an "effective amount" is one that prophylactically treats one or more symptoms and/or underlying causes of a disorder or disease. An effective amount can also be an amount that therapeutically treats one or more symptoms and/or underlying causes of a disorder or disease.

Interfering RNA: Interfering RNA (which can be interchangeably referred to as RNAi) or an interfering RNA sequence refers to double-stranded RNA that is capable of silencing, reducing, or inhibiting expression of a target gene by any mechanism of action now known or yet to be disclosed. For example, RNAi may act by mediating the degradation of mRNAs which are complementary to the sequence of the RNAi when the RNAi is in the same cell as the target gene. RNAi thus refers to both the double-stranded RNA formed by two complementary RNA strands or by a single, self-complementary strand. RNAi may have substantial or complete identity to the target gene or may comprise one or more mismatches upon alignment to the target gene. The sequence of the interfering RNA may correspond to the full length target gene, or any subsequence thereof. As described herein an RNAi is an interfering RNA sequence that is chemically synthesized as an oligoribonucleotide. An RNAi can be single stranded or double stranded. As described herein an shRNA is an RNAi molecule that is expressed from a DNA template using a promoter operably linked to the shRNA sequence. The shRNA can be expressed in vitro or expressed upon transfection of a cell with an expression vector comprising the shRNA and a cell specific promoter. A shRNA includes an RNAi and its complementary strand with a linker sequence between. The shRNA is transcribed as a single RNA molecule that forms a double stranded structure after transcription.

Nucleic acid synthesis and Purification: Methods for isolating RNA, synthesizing RNA, hybridizing nucleic acids, making and screening cDNA libraries, and performing PCR are well known in the art (see, e.g., Gubler and Hoffman, *Gene* 25, 263-269 (1983); Sambrook and Russell, *Molecular Cloning: A Laboratory Manual*, Cold Spring Harbor Laboratory Press, Cold Spring Harbor N.Y., (2001)) as are PCR methods (see, U.S. Pat. Nos. 4,683,195 and 4,683,202; *PCR Protocols: A Guide to Methods and Applications*, Innis et al, eds, (1990)). Expression libraries are also well known to those of skill in the art. Additional basic texts disclosing the general methods of use in this invention include Sambrook and Russell (2001) supra; Kriegler, *Gene Transfer and Expression: A Laboratory Manual* (1990); and *Current Protocols in Molecular Biology* (Ausubel et al., eds., 1994).

Operably Linked: A first nucleic acid sequence is operably linked with a second nucleic acid sequence when the first nucleic acid sequence is placed in such a way that it has an effect upon the second nucleic acid sequence. For instance, a promoter is operably linked to a coding sequence if the promoter affects the transcription or expression of the coding sequence. Operably linked DNA sequences may be contiguous, or they may operate at a distance.

Pharmaceutically acceptable carriers: The pharmaceutically acceptable carriers of use are conventional. Remington's Pharmaceutical Sciences, by E. W. Martin, Mack Publishing Co., Easton, Pa., 19th Edition, 1995, describes compositions and formulations suitable for pharmaceutical delivery of the compositions disclosed herein. In general, the nature of the carrier will depend on the particular mode of administration being employed. For instance, formulations intended for topical use include pharmaceutically and physiologically acceptable fluids such as water, physiological saline, balanced salt solutions, aqueous dextrose, glycerol or the like as a vehicle as well as other compounds that promote penetration into the skin.

In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Promoter: A promoter may be any of a number of nucleic acid control sequences that direct transcription of a nucleic acid. Typically, a eukaryotic promoter includes necessary nucleic acid sequences near the start site of transcription, such as, in the case of a polymerase II type promoter, a TATA element or any other specific DNA sequence that is recognized by one or more transcription factors. Expression by a promoter can be further modulated by enhancer or repressor elements. Numerous examples of promoters are available and well known to those of skill in the art. A nucleic acid comprising a promoter operably linked to a nucleic acid sequence that codes for a particular polypeptide can be termed an expression vector.

Quantification of gene expression: Methods known in the art for the detection and quantification of RNA expression in a sample include northern blotting and in situ hybridization (Parker and Barnes, *Methods in Molecular Biology* 106, 247-283 (1999); RNAse protection assays (Hod, *Biotechniques* 13, 852-854 (1992)); and PCR-based methods, such as reverse transcription polymerase chain reaction (RT-PCR) (Weis et al., *Trends in Genetics* 8, 263-264 (1992)). Representative methods for sequencing-based gene expression analysis include Serial Analysis of Gene Expression (SAGE), and gene expression analysis by massively parallel signature sequencing (MPSS). (See Mardis E R, *Annu Rev Genomics Hum Genet* 9, 387-402 (2008)).

For example: proteins can be detected and quantified through epitopes recognized by polyclonal and/or monoclonal antibodies used in methods such as ELISA, immunoblot assays, flow cytometric assays, immunohistochemical assays, radioimmunoassays, Western blot assays, an immunofluorescent assays, chemiluminescent assays and other polypeptide detection strategies. Proteins may also be detected by mass spectrometry assays (potentially coupled to immunoaffinity assays) including matrix-assisted laser desorption/ionization time-of-flight (MALDI-TOF) mass mapping and liquid chromatography/quadrupole time-of-flight electrospray ionization tandem mass spectrometry (LC/Q-TOF-ESI-MS/MS). Additionally, protein expression may be detected by tagging of proteins separated by two-dimensional polyacrylamide gel electrophoresis (2D-PAGE), (Kiernan et al, *Anal Biochem* 301, 49-56 (2002); Poutanen et al, *Mass Spectrom* 15, 1685-1692 (2001)) or any other method of detecting protein.

Recombinant: A recombinant nucleic acid is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls. in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino 5 acid sequences of greater than about 30 amino acids, the Blast 2 sequences function is employed using the default BLOSUM62 matrix set to default parameters, (gap existence cost of 11, and a per residue gap cost 5 of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity to a protein.

When aligning short peptides (fewer than around 30 amino acids), the alignment is performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, or 99% sequence identity to a protein. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Severe combined immunodeficiency (SCID) mouse: Refers to a strain of mice that is unable to undergo V(D)J recombination and therefore lack functional T cells and B cells. SCID mice also have an impaired ability to activate some components of the complement system. SCID mice are homozygous for the $Prkdc^{scid}$ mutation.

Subject: A living multicellular vertebrate organism, a category that includes, for example, mammals and birds. A mammal includes both human and non-human mammals, such as mice or non-human primates. In some examples, a subject is a patient, such as a patient that displays signs or symptoms of psoriasis. In other examples a subject is an experimental subject such as an immunocompromised mouse that has been grafted with human psoriatic skin tissue.

T cell: A type of lymphocyte (a subset of white blood cells) that plays a central role in cell-mediated immunity. T cells are distinguished from other types of lymphocytes, such as B cells and NK cells, by the presence of a special receptor on their cell surface that is called the T cell receptor (TCR). The thymus is generally believed to be the principal organ for T cell development. There are many different types of T cells and these types can be differentiated by the type of T cell receptor that they express ($\alpha/\beta$ or $\gamma/\delta$) by the expression of particular markers ($CD4^+$, $CD8^+$, etc.), by their function (helper T cells—abbreviated as Th, cytotoxic T cells—abbreviated as Tc or CTL, etc.) T cells of a particular group can be subtyped. For example, helper T cells can be differentiated further into Th1, Th2, Th17, and other cell types based on the types of factors expressed by the T cell as well as the function of the T cell.

Treating a disease: Inhibiting the full development of a disease or condition, for example, in a subject who has or is at risk for developing a disease such as psoriasis. Treatment refers to any therapeutic intervention that ameliorates a sign or symptom of a disease or pathological condition. The term "ameliorating," with reference to a disease or pathological condition, refers to any observable beneficial effect provided by a pharmaceutical composition. The beneficial effect can be evidenced, for example, by a delayed onset of clinical symptoms of the disease in a susceptible subject, a reduction in severity of some or all clinical symptoms of the disease, a slower progression of the disease or by other clinical or physiological parameters associated with a particular disease. A "prophylactic" treatment is a treatment administered to a subject who does not exhibit signs of a disease or exhibits only early signs for the purpose of decreasing the risk of developing pathology.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes. In one example described herein, the vector comprises a nucleic acid sequence that encodes CD4-AsiC-ROR2.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below.

RNAi based therapeutics

The concept of RNAi includes small-interfering RNA, which may interchangeably be referred to as RNAi and small hairpin RNA referred to as shRNA. An RNAi construct may be any interfering RNA with a duplex length of about 15-60, 15-50, or 15-40 nucleotides in length, more typically about 15-30, 15-25, or 18-23 nucleotides in length. Each complementary sequence of the double-stranded RNAi may be 15-60, 15-50, 15-40, 15-30, 15-25, or 18-23 nucleotides in length, but other noncomplementary sequences may be present. For example, RNAi duplexes may comprise 3' overhangs of 1 to 4 or more nucleotides and/or 5' phosphate termini comprising 1 to 4 or more nucleotides. An RNAi may be synthesized in any of a number of conformations. One skilled in the art would recognize the type of RNAi conformation to be used for a particular purpose. Examples of RNAi conformations include, but need not be limited to, a double-stranded polynucleotide molecule assembled from two separate stranded molecules, wherein one strand is the sense strand and the other is the complementary antisense strand; a double-stranded polynucleotide molecule assembled from a single-stranded molecule, where the sense and antisense regions are linked by a nucleic acid-based or non-nucleic acid-based linker; a double-stranded polynucleotide molecule with a hairpin secondary structure having complementary sense and antisense regions; or a circular single-stranded polynucleotide molecule with two or more loop structures and a stem having self-complementary sense and antisense regions. In the case of the circular polynucleotide, the polynucleotide may be processed either in vivo or in vitro to generate an active double-stranded RNAi molecule.

An RNAi can be chemically synthesized, may be encoded by a plasmid and transcribed, or may be vectored by a virus engineered to express the siRNA. A RNAi may be a single stranded molecule with complementary sequences that self-hybridize into duplexes with hairpin loops. RNAi can also be generated by cleavage of parent dsRNA through the use of an appropriate enzyme such as *E. coli* RNase III or Dicer (Yang et al, *Proc. Natl. Acad. Sci. USA* 99, 9942-9947 (2002); Calegari et al, *Proc. Natl. Acad. Sci. USA* 99, 14236-14240 (2002); Byrom et al, *Ambion Tech Notes* 10, 4-6 (2003); Kawasaki et al, *Nucleic Acids Res* 31, 981-987 (2003); Knight et al, *Science* 293, 2269-2271 (2001); and Robertson et al, *J Biol Chem* 243, 82-91 (1968)). A parent dsRNA may be any double stranded RNA duplex from which an RNAi may be produced, such as a full or partial mRNA transcript.

A mismatch motif may be any portion of a RNAi sequence that is not 100% complementary to its target sequence. A RNAi may have zero, one, two, or three or more mismatch regions. The mismatch regions may be contiguous or may be separated by any number of complementary nucleotides. The mismatch motifs or regions may comprise a single nucleotide or may comprise two or more consecutive nucleotides.

A RNAi molecule can inhibit the expression of a target gene, such as a gene involved in the development of psoriasis such as RORC2. The terms "silencing" or "reducing" may be used interchangeably with "inhibiting." To examine the extent of inhibition of expression by a siRNA, a RNAi of interest is added to a test sample and to a negative control sample to which the RNAi was not added. Preferably, a negative control sample is similar to the test sample. More preferably, the negative control sample is identical to the test sample. Examples of negative control samples include untreated samples, samples to which a siRNA-free buffer was added, or samples to which a negative control or mock RNAi was added. Expression in the test sample is then compared to expression in the negative control sample. Expression may be measured by the detection of any expression product known in the art or yet to be disclosed. Typical expression products that may be detected include RNA or protein.

RNAi molecules can be provided in several forms including, e.g., as one or more isolated RNAi duplexes, as longer double-stranded RNA (dsRNA), or as RNAi or dsRNA transcribed from a transcriptional cassette in a DNA plasmid. The RNAi sequences may have overhangs (as 3' or 5' overhangs as described in Elbashir et al, *Genes Dev* 15, 188 (2001) or Nykänen et al, *Cell* 107, 309 (2001)) or may lack overhangs (i.e., have blunt ends).

Expression vectors encoding one or more RNAi templates may be used to provide siRNA. RNAi can be transcribed as sequences that automatically fold into duplexes with hairpin loops from DNA templates in plasmids having RNA polymerase III transcriptional units, for example, based on the naturally occurring transcription units for small nuclear RNA U6 or human RNase P RNA H1 (Brummelkamp et al, *Science* 296, 550 (2002); Donzé et al, *Nucleic Acids Res* 30, e46 (2002); Paddison et al, *Genes Dev* 16, 948 (2002); Yu et al, *Proc Natl Acad Sci USA* 99, 6047 (2002); Lee et al, *Nat Biotech*, 20, 500 (2002); Miyagishi et al, *Nat Biotech* 20, 497 (2002); Paul et al, *Nat Biotech*, 20, 505 (2002); and Sui et al, *Proc Natl Acad Sci USA*, 99, 5515 (2002)).

Typically, a transcriptional unit or cassette will contain an RNA transcript promoter sequence, such as an H1-RNA or a U6 promoter, operably linked to a template for transcription of a desired RNAi sequence and a termination sequence, comprised of 2-3 uridine residues and a polythymidine (T5) sequence (polyadenylation signal) (Brummelkamp et al (2002) supra). The selected promoter can provide for constitutive or inducible transcription. Compositions and methods for DNA-directed transcription of RNA interference molecules are described in detail in U.S. Pat. No. 6,573,099. The transcriptional unit is incorporated into a plasmid or DNA vector from which the interfering RNA is transcribed. Plasmids suitable for in vivo delivery of genetic material for therapeutic purposes are described in detail in U.S. Pat. Nos. 5,962,428 and 5,910,488. The selected plasmid can provide for transient or stable delivery of a nucleic acid to a target cell. It will be apparent to those of skill in the art that plasmids originally designed to express desired gene sequences can be modified to contain a transcriptional unit cassette for transcription of siRNA.

A RNAi molecule may be chemically synthesized. In one example of chemical synthesis, a single-stranded nucleic acid that includes the RNAi duplex sequence can be synthesized using any of a variety of techniques known in the art, such as those described in Usman et al, *J Am Chem Soc*, 109, 7845 (1987); Scaringe et al, *Nucl Acids Res*, 18, 5433 (1990); Wincott et al, *Nucl Acids Res*, 23, 2677-2684 (1995); and Wincott et al, *Methods Mol Bio* 74, 59 (1997). Synthesis of the single-stranded nucleic acid makes use of common nucleic acid protecting and coupling groups, such as dimethoxytrityl at the 5'-end and phosphoramidites at the 3'-end. As a non-limiting example, small scale syntheses can be conducted on an *Applied Biosystems synthesizer using a* 0.2 micromolar scale protocol with a 2.5 min coupling step for 2'-O-methylated nucleotides. Alternatively, syntheses at the 0.2 micromolar scale can be performed on a 96-well plate synthesizer from Protogene. However, a larger or smaller scale of synthesis is encompassed by the invention, including any method of synthesis now known or yet to be disclosed. Suitable reagents for synthesis of the RNAi single-stranded molecules, methods for RNA deprotection, and methods for RNA purification are known to those of skill in the art.

An RNAi can also be synthesized via a tandem synthesis technique, wherein both strands are synthesized as a single continuous fragment or strand separated by a linker that is subsequently cleaved to provide separate fragments or strands that hybridize to form an RNAi duplex. The linker may be any linker, including a polynucleotide linker or a non-nucleotide linker. The tandem synthesis of RNAi can be readily adapted to both multiwell/multiplate synthesis platforms as well as large scale synthesis platforms employing batch reactors, synthesis columns, and the like. Alternatively, the RNAi can be assembled from two distinct single-stranded molecules, wherein one strand includes the sense strand and the other includes the antisense strand of the siRNA. For example, each strand can be synthesized separately and joined together by hybridization or ligation following synthesis and/or deprotection. Either the sense or the antisense strand may contain additional nucleotides that are not complementary to one another and do not form a double stranded siRNA. In certain other instances, the RNAi molecules can be synthesized as a single continuous fragment, where the self-complementary sense and antisense regions hybridize to form a RNAi duplex having hairpin secondary structure.

An RNAi molecule may comprise a duplex having two complementary strands that form a double-stranded region with least one modified nucleotide in the double-stranded region. The modified nucleotide may be on one strand or both. If the modified nucleotide is present on both strands, it may be in the same or different positions on each strand. A modified RNAi may be less immunostimulatory than a corresponding unmodified RNAi sequence, but retains the capability of silencing the expression of a target sequence.

Examples of modified nucleotides suitable for use in the present invention include, but are not limited to, ribonucleotides having a 2T-O-methyl (2'OMe), 2'-deoxy-2'-fluoro (2'F), 2'-deoxy, 5-C-methyl, 2'-O-(2-methoxyethyl) (MOE), 4'-thio, 2'-amino, or 2'-C-allyl group. Modified nucleotides having a conformation such as those described in the art, for example in Saenger, Principles of Nucleic Acid Structure, Springer-Verlag Ed. (1984), are also suitable for use in RNAi molecules. Other modified nucleotides include, without limitation: locked nucleic acid (LNA) nucleotides, G-clamp nucleotides, or nucleotide base analogs. LNA nucleotides include but need not be limited to 2'-O, 4'-C-methylene-(D-ribofuranosyl)nucleotides), 2'-O-(2-methoxyethyl) (MOE) nucleotides, 2'-methyl-thio-ethyl nucleotides, 2'-deoxy-2'-fluoro (2'F) nucleotides, 2'-deoxy-2'-chloro (2Cl) nucleotides, and 2'-azido nucleotides. A G-clamp nucleotide refers to a modified cytosine analog wherein the modifications confer the ability to hydrogen bond both Watson-Crick and Hoogsteen faces of a complementary guanine nucleotide within a duplex (Lin et al, *J Am Chem Soc*, 120, 8531-8532 (1998)). Nucleotide base analogs include for example, C-phenyl, C-naphthyl, other aromatic derivatives, inosine, azole carboxamides, and nitroazole derivatives such as 3-nitropyrrole, 4-nitroindole, 5-nitroindole, and 6-nitroindole (Loakes, *Nucl Acids Res*, 29, 2437-2447 (2001)).

A RNAi molecule may comprise one or more chemical modifications such as terminal cap moieties, phosphate backbone modifications, and the like. Examples of classes of terminal cap moieties include, without limitation, inverted deoxy abasic residues, glyceryl modifications, 4',5'-methylene nucleotides, 1-(β-D-erythrofuranosyl) nucleotides, 4'-thio nucleotides, carbocyclic nucleotides, 1,5-anhydrohexitol nucleotides, L-nucleotides, α-nucleotides, modified base nucleotides, threo pentofuranosyl nucleotides, acyclic 3',4'-seco nucleotides, acyclic 3,4-dihydroxybutyl nucleotides, acyclic 3,5-dihydroxypentyl nucleotides, 3'-3'-inverted nucleotide moieties, 3'-3'-inverted abasic moieties, 3'-2'-inverted nucleotide moieties, 3'-2'-inverted abasic moieties, 5'-5'-inverted nucleotide moieties, 5'-5'-inverted abasic moieties, 3'-5'-inverted deoxy abasic moieties, 5'-aminoalkyl phosphate, 1,3-diamino-2-propyl phosphate, 3 aminopropyl phosphate, 6-aminohexyl phosphate, 1,2-aminododecyl phosphate, hydroxypropyl phosphate, 1,4-butanediol phosphate, 3'-phosphoramidate, 5' phosphoramidate, hexylphosphate, aminohexyl phosphate, 3'-phosphate, 5'-amino, 3'-phosphorothioate, 5'-phosphorothioate, phosphorodithioate, and bridging or non-bridging methylphosphonate or 5'-mercapto moieties (see, e.g., U.S. Pat. No. 5,998,203; Beaucage et al, Tetrahedron 49, 1925 (1993)). Non-limiting examples of phosphate backbone modifications (i.e., resulting in modified internucleotide linkages) include phosphorothioate, phosphorodithioate, methylphosphonate, phosphotriester, morpholino, amidate, carbamate, carboxymethyl, acetamidate, polyamide, sulfonate, sulfonamide, sulfamate, formacetal, thioformacetal, and alkylsilyl substitutions (see, e.g., Hunziker et al, Modern Synthetic Methods, VCH, 331-417 (1995); Mesmaeker et al, Antisense Research, ACS, 24-39 (1994)). Such chemical modifications can occur at the 5'-end and/or 3'-end of the sense strand, antisense strand, or both strands of the siRNA.

The sense and/or antisense strand of an RNAi may comprise a 3'-terminal overhang having 1 to 4 or more 2'-deoxyribonucleotides and/or any combination of modified and unmodified nucleotides. Additional examples of modified nucleotides and types of chemical modifications that can be introduced into the modified RNAi molecules of the present invention are described, e.g., in UK Patent No. GB 2,397,818 B and U.S. Patent Publication Nos. 20040192626 and 20050282188.

An RNAi molecule may comprise one or more non-nucleotides in one or both strands of the siRNA. A nonnucleotide may be any subunit, functional group, or other molecular entity capable of being incorporated into a nucleic acid chain in the place of one or more nucleotide units that is not or does not comprise a commonly recognized nucleotide base such as adenosine, guanine, cytosine, uracil, or thymine, such as a sugar or phosphate.

Chemical modification of the RNAi may also comprise attaching a conjugate to the RNAi molecule. The conjugate can be attached at the 5'- and/or the 3'-end of the sense and/or the antisense strand of the RNAi via a covalent attachment such as a nucleic acid or non-nucleic acid linker. The conjugate can also be attached to the RNAi through a carbamate group or other linking group (see, e.g., U.S. Patent Publication Nos. 20050074771, 20050043219, and 20050158727). A conjugate may be added to the RNAi for any of a number of purposes. For example, the conjugate may be a molecular entity that facilitates the delivery of the RNAi into a cell or the conjugate a molecule that comprises a drug or label. Examples of conjugate molecules suitable for attachment to the RNAi of the present invention include, without limitation, steroids such as cholesterol, glycols such as polyethylene glycol (PEG), human serum albumin (HSA), fatty acids, carotenoids, terpenes, bile acids, folates (e.g., folic acid, folate analogs and derivatives thereof), sugars (e.g., galactose, galactosamine, N-acetyl galactosamine, glucose, mannose, fructose, fucose, etc.), phospholipids, peptides, ligands for cellular receptors capable of mediating cellular uptake, and combinations thereof (see, e.g., U.S. Patent Publication Nos. 20030130186, 20040110296, and 20040249178; U.S. Pat. No. 6,753,423). Other examples include the lipophilic moiety, vitamin, polymer, peptide, protein, nucleic acid, small molecule, oligosaccharide, carbohydrate cluster, intercalator, minor groove binder, cleaving agent, and cross-linking agent conjugate molecules described in U.S. Patent Publication Nos. 20050119470 and 20050107325. Other examples include the 2'-O-alkyl amine, 2'-O-alkoxyalkyl amine, polyamine, C5-cationic modified pyrimidine, cationic peptide, guanidinium group, amidininium group, cationic amino acid conjugate molecules described in U.S. Patent Publication No. 20050153337. Additional examples of conjugate molecules include a hydrophobic group, a membrane active compound, a cell penetrating compound, a cell targeting signal, an interaction modifier, or a steric stabilizer as described in U.S. Patent Publication No. 20040167090. Further examples include the conjugate molecules described in U.S. Patent Publication No. 20050239739.

The type of conjugate used and the extent of conjugation to the RNAi can be evaluated for improved pharmacokinetic profiles, bioavailability, and/or stability of the RNAi while retaining activity. As such, one skilled in the art can screen RNAi molecules having various conjugates attached thereto to identify RNAi conjugates having improved properties using any of a variety of well-known in vitro cell culture or in vivo animal models.

An RNAi may be incorporated into a carrier systems containing the RNAi molecules described herein. The carrier system may be a lipid-based carrier system such as a stabilized nucleic acid-lipid particle (e.g., SNALP or SPLP), cationic lipid or liposome nucleic acid complexes (i.e., lipoplexes), a liposome, a micelle, a virosome, or a mixture thereof. In other embodiments, the carrier system is a polymer-based carrier system such as a cationic polymer-nucleic acid complex (i.e., polyplex). In additional embodiments, the carrier system is a cyclodextrin-based carrier system such as a cyclodextrin polymer-nucleic acid complex (see US Patent Application Publication 20070218122). In further embodiments, the carrier system is a protein-based carrier system such as a cationic peptide-nucleic acid complex. A RNAi molecule may also be delivered as naked siRNA.

Pharmaceutical Compositions:

The compounds disclosed herein may be included in pharmaceutical compositions (including therapeutic and prophylactic formulations), typically combined together with one or more pharmaceutically acceptable vehicles or carriers and, optionally, other therapeutic ingredients (for example, antibodies and/or anti-inflammatory compounds). The compositions disclosed herein may be advantageously combined and/or used in combination with other agents used in order to treat psoriasis.

Such pharmaceutical compositions can be administered to subjects by a variety of mucosal administration modes, including by oral, rectal, intranasal, intrapulmonary, transdermal, or by topical delivery to the skin.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin), and reducing agents (for example, glutathione) can be included.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres, and films for direct application to a mucosal surface such as skin.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanoparticles prepared from a suitable polymer, for example, 5 isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time.

The pharmaceutical compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like. Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acidco-glycolic acid), poly(D-lactic acid-co-glycolic acid), and poly(L-lactic acid-coglycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water soluble peptides.

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

RNAi/Aptamer Chimeras

Aptamers are single stranded oligonucleotides selected from random sequence libraries with high affinity and specificity to the target molecules (Zhou J et al, *Mol Ther* 21, 192-200 (2013); Ni X et al, *Curr Med Chem* 18, 4206-4214 (2011); both of which are incorporated by reference herein). Besides being effective therapeutic agents, aptamers have been actively exploited for targeted delivery of drugs including RNAi Zhou J et al, *Front Genet* 3, 234 (2012); incorporated by reference herein). In theory, due to their high specificity and affinity, aptamers can deliver RNAi into any cell type provided the cells express the ligand for aptamer to bind. Aptamer RNAi chimeras, first described in McNamara J O et al, *Nat Biotechnol* 24, 1005-1015 (2006) (which is incorporated by reference herein) has been used to deliver RNAi into prostate cancer cells. An aptamer-RNAi chimera with an aptamer that binds specifically to HIV envelope protein and expressed by viral infected T cells and RNAi to viral genes and successfully suppressed HIV replication in HIV infected human CD4$^+$ T cells (Zhou J et al, *Mol Ther* 16, 1481-1489 (2008); incorporated by reference herein). A CD4 aptamer-RNAi chimera targeting CCR5, gag and vif was delivered to infected human CD4$^+$ T cells, suppressed the expression of the targeted genes and killed HIV (Wheeler L A et al, *J Clin Invest* 121 2401-2412 (2011) and Wheeler L A et al, *Mol Ther* 21, 1378-1389 (2013); both of which are incorporated by reference herein.

IL-17 and Disease

Disclosed herein is a CD4 aptamer-shRNA chimera specific to RORγt to suppress T helper 17 (Th17) cells that has the potential to be a Th17 specific therapeutic agent in Th17 mediated inflammatory diseases. Increasing evidence indicates that Th17 cells and their released cytokines play a critical role in the pathogenesis of autoimmune and inflammatory diseases (Miossec P et al, *Nat Rev Drug Discov* 11, 763-776 (2012); incorporated by reference herein). Th17 cells preferentially express and produce IL-17A, IL-17F, IL-21, and IL-22. Th17 cells and their secreted cytokines are considered to account for initiation and maintenance of several autoimmune and inflammatory disorders (van Hamburg J P et al, *Ann Rheum Dis* 72, 1700-1707 (2013); van Hamburg J P et al, *Arthritis Rheum* 63, 73-83 (2011); Cascao R et al, *Arth Res Ther* 12, R196 (2010); all of which are incorporated by reference herein. Blocking IL-17A activity has been proven to be highly effective to treat immune mediated inflammatory disease models and clinical trials with blocking IL-17 are ongoing with promising results to treat inflammatory diseases (Chu C Q et al, *Ann Rheum Dis* 62, 983-990 (2003); Lubberts E, *Cytokine* 41, 84-91 (2008); and Genovese M C et al, *Arthritis Rheum* 62, 929-939 (2010); all of which are incorporated by reference herein. However, IL-17A and IL-17F are also produced by many other innate immune cells and are important cytokines in host defense (Korn T et al, *Ann Rev Immunol* 27, 485-517 (2009); incorporated by reference herein). Moreover, it is Th17 cells that are detrimental and are to be blocked for therapeutic purposes. Therefore, it is highly desirable to narrow the target to Th17 cells and spare IL-17 cytokines produced by innate immune cells from being blocked.

Psoriasis and IL-17

Psoriasis is common inflammatory skin disease affecting up to 2% of the population (Nestle F O et al, *N Engl J Med* 361, 496-509 (2009); incorporated by reference herein) with significant co-morbidities (Gelfand J M et al, *J Am Med Assoc* 296, 1735-1741 (2006) and Neimann A L et al, *J Am Acad Derm* 55, 829-835 (2006); both of which are incorporated by reference herein). Psoriasis can have profound psychological effects with quality-of-life impairment to a similar or worse extent to that seen in chronic diseases such as cancer, arthritis and depression, resulting in decreased productivity and social functioning (Feldman S R et al, *J Am Acad Derm* 37, 564-569 (1997); incorporated by reference herein). While psoriasis patients with severe disease require systemic therapy the majority (~75%) of patients has mild to moderate disease that is better managed with topical agents and/or phototherapy.

The Th17 subset of helper T cells play a critical role in the pathogenesis of psoriasis. This has been demonstrated in clinical trials of the monoclonal antibody ustekinumab, which targets the common p40 subunit of IL-23 and IL-12. Ustekinumab shows high efficacy in psoriasis and has been approved by FDA for treating psoriasis. In addition, several monoclonal antibodies that specifically target the common p19 subunit of IL-23, IL-17A, and the IL-17 receptor are in various stages of clinical trials for treating psoriasis (reviewed in Garber K, *Nat Biotechnol* 30, 475-477 (2012); incorporated by reference herein.

IL-17 and other members of IL-17 family are produced by many other cell types, in particular, innate immune cells which play an important role in host defense. For example, IL-17 secreting γ/δ T cells are critical for skin defense to infections (Gray E E et al, *J Immunol* 185, 6091-6095 (2011) and Sumaria N et al, *J Exp Med* 208, 505-518 (2011); both of which are incorporated by reference herein.) Furthermore, studies using gene knockout mice demonstrate that γ/δ T cells secreting IL-17, but not IL-22 or IL-21, nor α/β T cells are essential for skin defense to *Staphylococcus aureus* infection. IL-17 secreting γ/δ T cells are present in psoriatic lesions but their role in the pathogenesis of psoriasis has been questioned (Cai Y et al, *Immunity* 35, 596-610 (2011); incorporated by reference herein). Systemic blockade of IL-17 potentially results in an increased risk of infection.

Because γ/δ T cells do not express CD4, the disclosed composition will selectively target on Th17 cells and spare γ/δ T cells. Therefore a non-systemic approach to the treatment of psoriasis that selectively targets Th17 cells will be highly advantageous.

Aptamer-RNAi chimeras to target RORγt

RORγt is a nuclear transcription factor. The intracellular location of RORγt makes it an undruggable target by monoclonal antibodies. It was recently reported that digoxin and its derivatives can suppress Th17 cells by antagonizing RORγt (Huh J R et al, *Nature* 472, 486-490 (2011) and Fujita-Sato S et al, *J Biol Chem* 286, 31409-31417 (2011); both of which are incorporated by reference herein). However, the narrow therapeutic index of digoxin and its effects on cardiac rhythm (Bhatia S J and Smith T W, *J Cardiac Surg* 2, 453-465 (1987); incorporated by reference herein) are likely to limit its use for therapy in psoriasis. An approach using RNAi to directly target RORγt expression would be more specific with the potential for fewer side effects. An RNAi specific to RORγt can be delivered intracellularly, and would be easily manufactured.

RNAi based therapeutics have been evaluated in several preclinical to phase II clinical trials for diseases ranging from asthma and cancer to viral infections (Vaishnaw A K et al, *Silence* 1, 14 (2010), incorporated by reference herein. However, the major hurdle for widespread use of RNAi as therapeutic agents is the inefficient intracellular RNAi delivery to target sites.

Aptamers are single-stranded nucleic acids that bind to molecular targets with high affinity and specificity due to their stable three dimensional shapes (Bouchard P R et al, *Ann Rev Pharm Tox* 50, 237-257 (2010); incorporated by reference herein). Aptamers are typically 20-100 nucleotides in length and can be selected from libraries of up to $10^{15}$ individual sequences to bind with high affinity to a wide array of proteins and/or to modulate protein function in a manner analogous to antibodies (Keefe A D et al, *Nat Rev Drug Discovery* 9, 537-550 (2010); incorporated by reference herein). Aptamers more readily allow chemical substitutions and other modifications and aptamers elicit minimal immunogenicity relative to antibodies. Their relatively small physical size allows better tissue penetration than antibodies. Aptamers allow for a straightforward chemical synthesis, which in turn allows easier modification and rapid in vitro selection. Pegaptanib, an RNA aptamer specific for VEGF, has been approved by FDA to treat wet age-related macular degeneration (Campa C and Harding S P, *Curr Drug Targets* 12, 173-181 (2011); incorporated by reference herein). Other aptamers are being explored for therapeutic purposes.

Use of aptamers as drug delivery devices has been investigated extensively. Aptamer-RNAi chimeras have been described in, for example McNamara J O et al, *Nature Biotechnology* 24, 1005-1015 (2006), which is incorporated by reference herein. In that example, a prostate specific membrane antigen aptamer was conjugated to a polo-like kinase-1 RNAi and used to suppress tumor growth. To date, a variety of aptamer-RNAi chimeras have been developed and tested in pre-clinical models for therapy in viral infections and tumors. For instance, a human CD4 aptamer-RNAi to CCR5 chimera can be used to inhibit HIV replication in HIV infected CD4+T cells in vivo in humanized mice (Wheeler L A et al, *J Clin Invest* 121, 2401-2412 (2011); incorporated by reference herein.

A chimera comprising a gp120 specific aptamer and a tat/rev RNAi has been constructed. When injected systemically using a Hu-scid mouse model of HIV infection, this composition inhibits HIV replication and prevents CD4+ T cells from being depleted. Neff C P et al, *Science Transl Med* 3, 66ra66 (2011); incorporated by reference herein.

Treatment of Psoriasis

The administration of the disclosed compounds and pharmaceutical compositions can be for prophylactic or therapeutic purposes. When provided prophylactically, the compound is provided in advance of any symptom. The prophylactic administration of the compound serves to prevent or ameliorate any subsequent disease process. When provided therapeutically, the compound is provided at or after the onset of a symptom of psoriasis.

For prophylactic and therapeutic purposes, the compound can be administered to the subject topically or via another mucosal delivery over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models (for example, immunologic and histopathologic assays).

Using such models, only ordinary calculations and adjustments are required to determine an appropriate concentration and dose to administer a therapeutically effective amount of the compound (for example, amounts that are effective to elicit a desired immune response or alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A nonlimiting range for a therapeutically effective amount of a compound and/or other biologically active agent within the methods and formulations of the disclosure is about 0.01 mg/kg body weight to about 100 mg/kg body weight, such as about 0.05 mg/kg to about 50 mg/kg body weight, or about 0.5 mg/kg to about 5 mg/kg body weight. Dosage can be varied to maintain a desired concentration at a target site (for example, psoriatic skin lesions). Dosage can also be adjusted based on the release rate of the administered formulation, for example, the release rate of a powder, gel, liquid, cream, lotion, or other topical formulation.

The instant disclosure also includes kits, packages and multi-container units containing the herein described pharmaceutical compositions, active ingredients, and/or devices and consumables that facilitate the administration the same for use in the prevention and treatment of diseases and other conditions in mammalian subjects.

In one example, this component is formulated in a pharmaceutical preparation for delivery to a subject. The conjugate is optionally contained in a bulk dispensing container or unit or multiunit dosage form. Optional dispensing devices can be provided, for example a spray or tube applicator. Packaging materials optionally include a label or instruction indicating for what treatment purposes and/or in what manner the pharmaceutical agent packaged therewith can be used.

EXAMPLES

Example 1

Synthesis of CD4 Aptamer-RORγ shRNA Chimera

Chimera synthesis was modified from previously described methods (Wheeler et al, 2011 supra; Zhou J and Rossi J J, *Methods Mol Biol* 721, 355-371 (2011); Ni X et al, *J Clin Invest* 121, 2383-2390 (2011); Davis K A, *Nuc Acids Res* 26, 3915-3924 (1998); all of which are incorporated by reference herein). A cDNA Template with a T7 promoter used for synthesis of the chimera was synthesized with Pfu DNA polymerase (Thermo Fisher Scientific) and purified with QIAquick® Gel purification kit (Qiagen). The sequence of the cDNA was verified by DNA sequencing. The RNA CD4 aptamer—shRNA chimera was transcribed using T7 polymerase in vitro using a DuraScribe® kit (Illumina). 2'-F-dCTP and 2'-F-dUTP were incorporated to enhance RNase resistance and Cy3-CTP (GE) was incorporated (Cy3-CTP/2T-F-dCTP ratio=1/9) for visualization. The chimera was phenol extracted and precipitated with sodium acetate/ethanol. After resuspension, the chimera was resolved on a 6% dPAGE gel and visualized using Cy3 scanning and ethidium bromide staining. It was then purified with G25 column (GE). The sequences of the chimeras of CD4 or mock CD4 aptamer—shRNAs against retinoic related orphan receptor (ROR)γ t and CCR5 or scrambled shRNA are shown in the sequence listing above.

In order to investigate if the CD4 aptamer shRNA chimera transcribed in vitro is the substrate for the endoribonuclease Dicer that processes longer endogenous RNA precursors into short RNA as an intracellular step of the RNAi pathway, Dicer cleavage of the chimera was assayed in vitro with a recombinant human Dicer kit (Genlantis) according to the manufacturer's instructions.

T Lymphocyte Cell Lines and T-Enriched PBMC's

Karpas 299 cells (described in Zhang P et al, *Lab Invest* 89, 1423-1432 (2009); incorporated by reference herein) were maintained in RPMI1640 containing 10% FBS. For evaluation of Cy3-labeled chimera internalization, Karpas 299 cells were incubated with 200 nM chimera overnight. For analysis of the function of chimeras in silencing RORγt and IL-17 production, Karpas 299 cells were incubated with the chimera for 72 h. Fresh PMBCs from healthy donors were isolated by Ficoll (GE) density centrifugation and cultured in RPMI 1640 medium containing 10% human AB serum. T enriched PBMCs were prepared by adding anti-CD11c, CD11b, CD19, CD56 and immnunomagnetic beads to PBMCs (BD Bioscience) and purified CD4$^+$ primary T cells are derived by removing CD8$^+$ T cell from T enriched PBMCs with anti-CD8 and immnunomagnetic beads.

Fluorescent Microscopy and Flow Cytometry

Internalization of the synthesized chimera was determined by incubating 200 nM or 1 μM Cy3-labeled chimera with Karpas 299 cells or T-cell enriched PBMC overnight. The cells were stained with FITC-anti-CD4 (BioLegend) and analyzed by confocal microscopy. T-cell enriched PBMCs were stimulated with anti-CD3/CD28 conjugated to MACS beads for 5 days. For Th1 cells, IL-12 (10 ng/ml) was added; for Th2 cells, IL-4 (10 ng/ml) and anti-human IFN-γ (10 μg/ml) were added; for Th17 cells, LPS (100 ng/ml) was added in the culture. PMA (50 ng/ml) and Ionomycin (500 ng/ml) were added 5 h prior to harvest for intracellular staining. Intracellular staining for RORγt and IL-17A was performed with PE-anti-mouse/human RORγt and PE-anti human IL-17A (eBioscience); staining for IFN-γ and IL-4 was performed with PE-anti-human IFN-γ and PE-anti-human IL-4 (BioLegend) and analyzed by flow cytometry.

Real-Time PCR

Real-time PCR was performed as described in Yomogida K et al, *Cytokine* 58, 431-436 (2012); incorporated by reference herein. The probe and primers mixes for RORC2 (Hs01076112), TBX21 (Hs00203436), GATA3 (Hs00231122) and GUSB (Hs9999908) were purchased from Thermo Fisher Scientific. MRNA levels for RORC, TBX21 and GATA3 were normalized by GUSB.

Quantification of Cytokines

IL-17A levels in the supernatant were quantified by ELISA (eBiosciences) as described in Yomogida K et al, *Cytokine* 63, 6-9 (2013); incorporated by reference herein. Karpas 299 cells were incubated with 50 ng/ml PMA and additional 40 mM sodium chloride for 48 h prior to harvesting the supernatant. T-cell enriched PBMCs were activated with biotinylated antibodies against human CD3 and CD28, conjugated to anti-biotin MACS beads (Miltenyi Biotec Inc.) and 100 ng/ml lipopolysaccharide (LPS) 48 h prior to collecting the supernatant.

Statistics

Data are presented as mean±SD. Data of real-time PCR, ELISA and flow cytometry were analyzed by one-way ANOVA followed by Dunnett comparison test. P value<0.05 was considered significant.

Example 2

CD4 Aptamer-RORγt shRNA Chimera was Specifically Internalized into Human CD4$^+$ T Cells An RNA aptamer that was identified by SELEX as able to specifically bind cellular membrane proteins with high-affinity is described in Bouchard P R et al, *Ann Rev Pharmacol Toxicol* 50, 237-257 (2010); incorporated by reference herein. It is also known that CD4 RNA aptamers can conjugate and deliver siRNAs/shRNAs targeting CCR5 and HIV gp120 gene into the T cells that express CD4 (Jayasena et al, U.S. Pat. No. 5,869,641 (1999); incorporated by reference herein). Described herein is the generation of a cDNA template that encodes a CD4 aptamer, a RORγt shRNA sense chain, a loop and a RORγt shRNA antisense chain. The cDNA sequence was verified by sequencing. RNA from the construct (CD4-AshR-RORγt) was transcribed as a single molecule in vitro by T7 polymerase transcription.

Figure 1A:
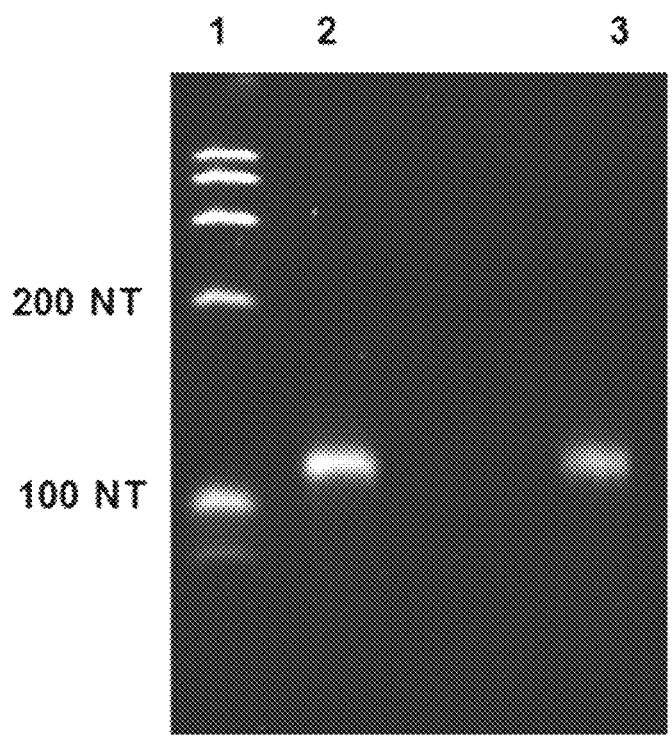
FIG. 1A is an image of a gel showing the indicated chimeras in vitro transcribed by T7 RNA polymerase analyzed by denatured PAGE and visualized by ethidium bromide staining. Lane 1, ssRNA ladder; Lane 2, CD4-AshR-RORγt chimera (SEQ ID NO: 1); Lane 3, mock-CD4-AshR-RORγt chimera (SEQ ID NO: 2).
Figure 1B:
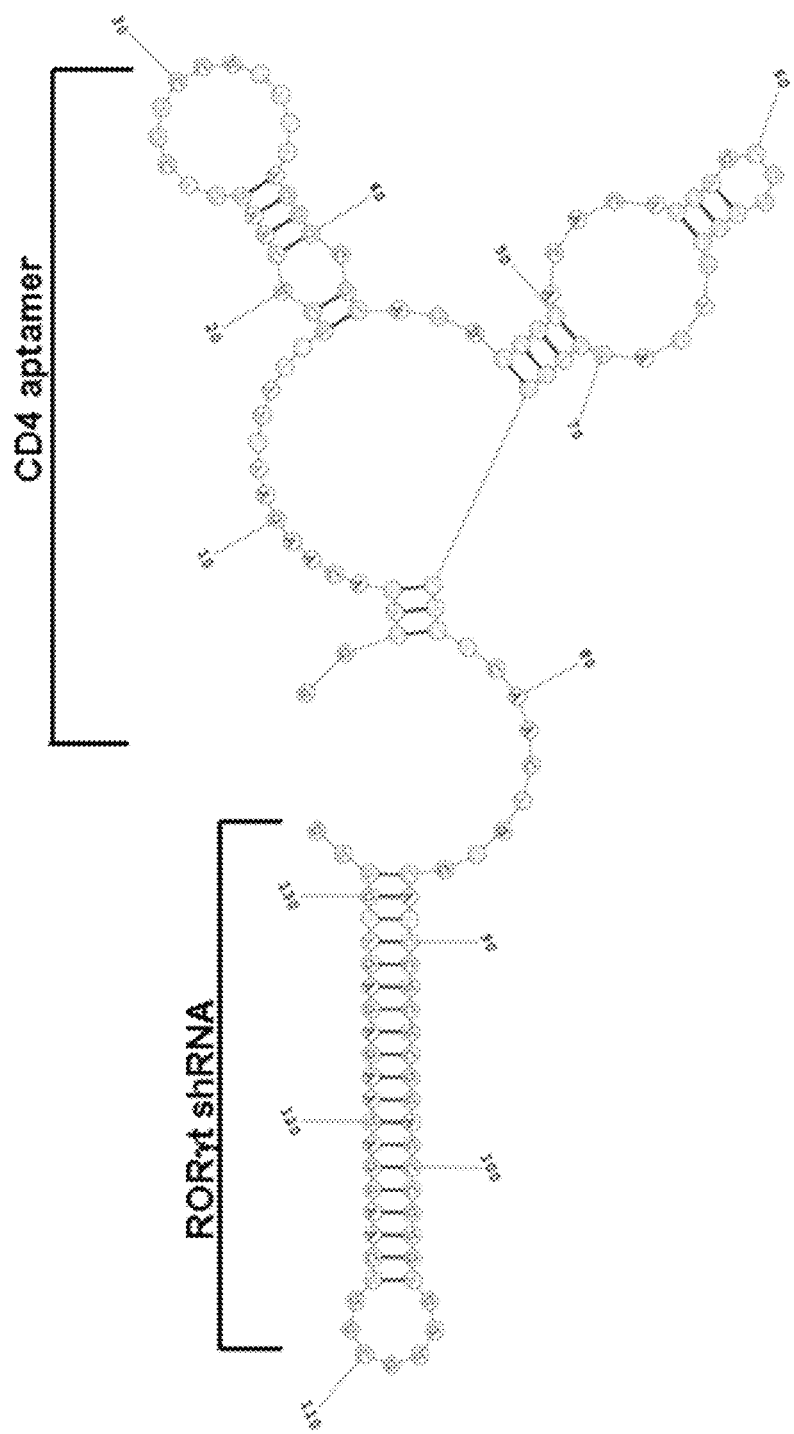
FIG. 1B is a diagram of the predicted secondary structure of CD4-AshR-RORγt chimera of SEQ ID NO: 1. The CD4 aptamer (clone 9 in Davis K A et al, *Nuc Acids Res* 26, 3915-3924 (1998); incorporated by reference herein) responsible for binding to CD4 is outlined. The shRNA portion of the chimera consists of targeted RORγt RNAi with 2 overhang nucleotides at its 3'end and a 7 nucleotide loop.
Figure 1C:
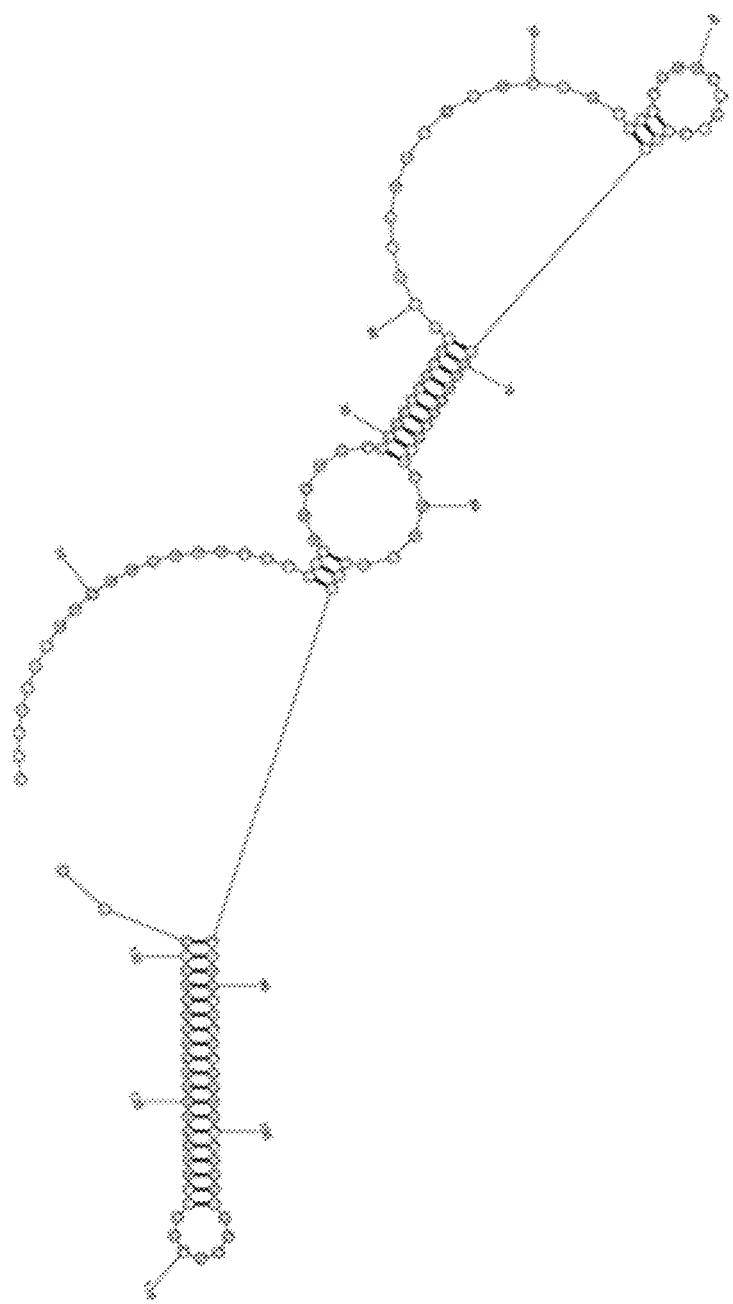
FIG. 1C is a diagram of the mock-CD4-AshR-RORγt chimera of SEQ ID NO: 2
Figure 2A:
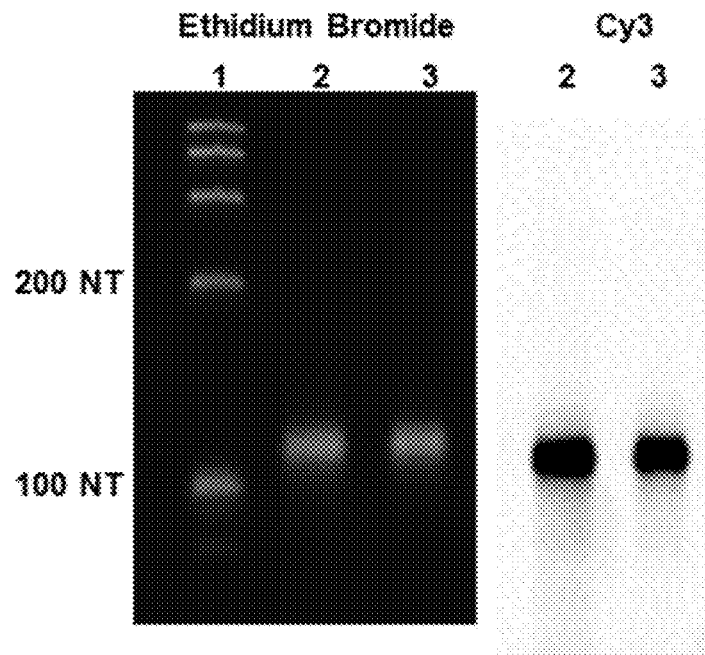
FIG. 2A is an image of two gels showing CD4- and mock-CD4-AshR-RORγt chimeras labeled by incorporating Cy3-CTP during in vitro transcription. Cy3 scanning (right panel) showed strong Cy3-signaling bands that were at an appropriate size of transcripts shown in ethidium bromide imaging (left panel). Lane 1, ssRNA ladder; Lane 2, CD4-AshR-RORγt chimera; Lane 3, mock-CD4-AshR-RORγt chimera.
Figure 2B:
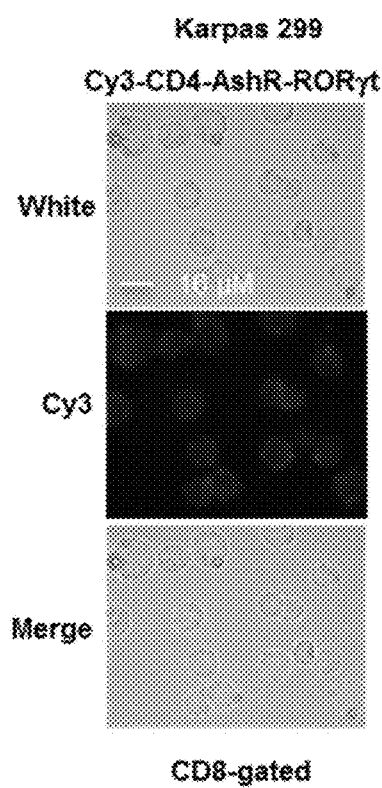
FIG. 2B is a set of three images showing uptake of Cy3-labeled CD4-AshR-RORγt chimera by the CD4+ human T cell line Karpas 299.
Figure 2C:
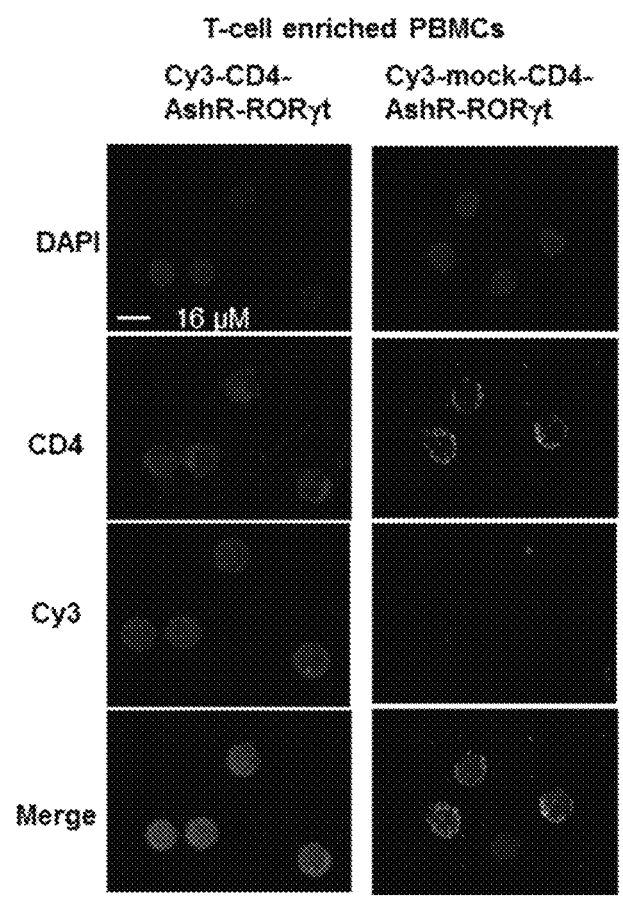
FIG. 2C is a set of six images showing uptake of Cy3 labeled CD4-AshR-RORγt chimera into CD4+ T cells in PBMCs (left panels). Note no uptake of Cy3 labeled mock CD4-AshR-RORγt chimera in the right panels.
Figure 2D:
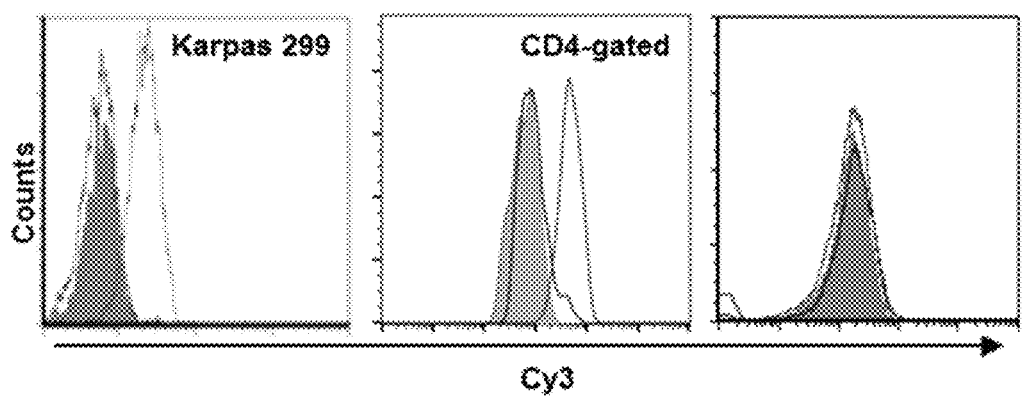
FIG. 2D is a set of three flow cytometry plots showing that Cy3-labeled CD4-AshR-RORγt chimera was significantly internalized in CD4+ Karpas 299 cells and CD4+ T cells but not in CD8+ T cells. There is no uptake of Cy3-labeled mock-CD4-AshR-RORγt chimera by Karpas 299 cells or T-cell enriched PBMCs. Gray: PBS; Red line: Cy3-labeled CD4-AshR-RORγt chimera; Blue line: Cy3-labeled mock-CD4-AshR-RORγt chimera (representative of 2-5 experiments)

A mock CD4 aptamer (SEQ ID NO: 2) was created using scrambled sequence. Both CD4-AshR-RORγt and mock-CD4-AshR-RORγt chimeras are 133 nucleotides in length (FIG. 1A). The predicted secondary structures of CD4-AshR-RORγt (FIG. 1B) and mock CD4-AshR-RORγt chimeras (FIG. 1C). Similarly, CD4 aptamer-CCR5 shRNA (CD4-AshR-CCR5) and CD4 aptamer-scrambled shRNA (CD4-AshR-scrambled) chimeras were generated as negative controls for RORγt shRNA. All of the chimeras incorporated 2'-F-CTP and 2'-F-UTP for enhanced resistance to RNase. In order to track internalization of the chimeras, two Cy3-CTPs were incorporated into each chimera as determined by spectophotometric analysis. A strong fluorochrome signal was readily detected by fluorescent gel scanning (FIG. 2A). Consistent with the characteristic of specifically and effectively delivering, the Cy3-labeled CD4-AshR-RORγt entered human CD4$^+$ T cell line, Karpas 299 cells and CD4$^+$ T cells in PBMC, as assessed with fluorescent confocal microscope and flow cytometric analysis (FIGS. 2B, 2C and 2D). In contrast, Cy3-labeled mock CD4-AshR-RORγt, in which the sequence of CD4 aptamer was scrambled, was unable to be internalized into Karpas 299, nor in CD4$^+$ T cells (FIG. 2D). Only a negligible amount of CD4 aptamer or CD4 aptamer conjugated to siRNAs is up-taken by CD8$^+$ T cells (FIG. 2D). These data suggest that the synthesized CD4 aptamer-shRNA chimera can be uniquely and sufficiently transferred into the CD4$^+$ human T cells.

Several strategies have been exploited to link an RNAi to an aptamer (Dassie J P et al, *Ther Deliv* 4, 1527-1546 (2013); incorporated by reference herein). Aptamer-RNAi chimeras linking an aptamer with an RNAi directly without using a linker sequence provides effective and specific delivery of RNAi into target cells. To make an aptamer-RNAi chimera, an aptamer-siRNA-sense strand is transcribed then is annealed to the separately synthesized antisense of siRNA. It was found that the annealing efficiency of antisense to sense strand linked to the aptamer is not consistent. Whereas, aptamer-shRNA chimera has a unique advantage being synthesized as a single RNA strand which does not require annealing with other RNAs. High yield production of aptamer-shRNA as a single molecule can be consistently achieved. This is particularly important for large scale of production of aptamer-shRNA for in vivo use. Moreover, the RNAi moiety of aptamer-shRNA chimera folds into a short hairpin structure (FIGS. 1B and C) which closely resembles endogenous microRNA. This has been demonstrated to be more readily processed by the RNAi machinery.

Example 3

Figure 1D:
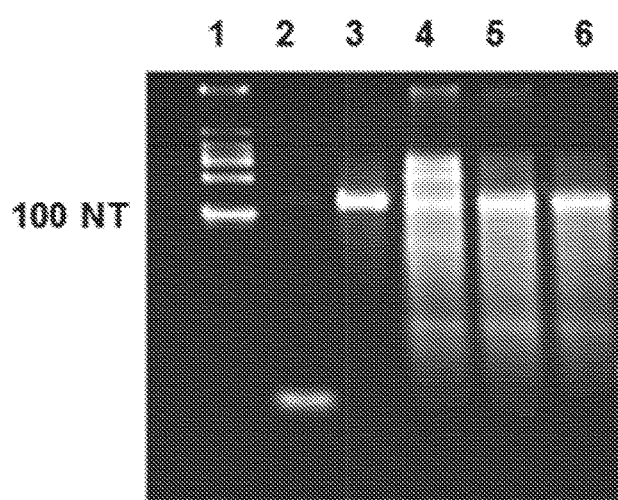
FIG. 1D is an image of a gel resulting from a cleavage analysis of synthesized chimeras by Dicer. Lane 1, ssRNA ladder; Lane 2, antisense RNAi to RORγt; Lane 3, intact CD4-AshR-RORγt chimera; Lanes 4-6 include chimeras that were digested with Dicer: Lane 4, Mock CD4-AshR-RORγt chimera (SEQ ID NO: 2); Lane 5, CD4-AshR-ROγt chimera (SEQ ID NO: 1); Lane 6, CD4-AshR-scrambled control chimera SEQ ID NO: 3.

A CD4-AshR-RORγt Chimera Significantly Silences RORγt Expression in Human CD4+ T Cells Intracellular small hairpin RNA is cleaved into 21-25 nucleotide double stranded RNA by Dicer and then the guide strand of the resulting duplexes are processed to the RNA-induced silencing complex (RISC) to degrade the complementary mRNA. Consistent with this, as shown in the FIGS. 1A and D, the size of CD4-AshR-RORγt chimera produced in vitro by T7 RNA polymerase transcription was originally 133 nucleotides in length. The shRNA moiety of CD4-AshR-RORγt chimera was released into short paired double stranded RNA after cleavage by Dicer (FIG. 1D). To confirm the silencing effect on specific gene expression, the level of RORγt mRNA was reduced by CD4-AshR-RORγt in a concentration-dependent fashion in the CD4+ Karpas 299 cells and T cell-enriched PBMCs, but not by mock CD4-AshR-RORγt, CD4-AshR-scrambled control, or CD4-AshR-CCR5 (FIG. 3A-3C), as assayed by quantitative real-time PCR. This was further demonstrated by intracellular RORγt staining with flow cytometry (FIG. 3D-F). The suppressive effect of CD4-AshR-RORγt delivered specific shRNA on RORγt expression is consistent with specific siRNAs transfected by lipid transfection agents (Burgler S et al, *J Immunol* 184, 6161-6169 (2010); incorporated by reference herein). In contrast, expression of TBX21 and GATA3 was not altered by CD4-AshR-RORγt (FIG. 3C). These data demonstrated that CD4-AshR-RORγt specifically suppressed RORγt gene expression.

Example 4

A CD4-AshR-RORγt Chimera Significantly Inhibits IL17 Production by CD4+ Human T Cells Down-regulation of RORγt function by its antagonists like digoxin derivatives could result in decrease of both Th17 cells and IL17 production (Huh J R (2011) supra.) As shown in FIG. 4A-D, consistent with decreased RORγt, CD4-AshR-RORγt exerted a concentration-dependent suppression of IL-17A production in CD4+ Karpas 299 cells and T cell-enriched PBMC. In parallel with altered secretion of IL-17A, intracellular IL-17A staining is significantly impaired by CD4-AshR-RORγt, whereas mock CD4-AshR-RORγt, CD4-AshR-scrambled control or CD4-AshR-CCR5 showed no effect. As shown in the FIG. 4E-H, the intracellular staining for IFN-γ and IL-4 was not changed by CD4-AshR-RORγt, suggesting it did not affect the synthesis of Th1 or Th2 cytokines. This further confirmed that RORγt is a valid target for regulating Th17 cell differentiation and IL-17 production.

The results disclosed herein show that a CD4 aptamer can serve as a delivery vehicle for shRNA that targets a specific gene in CD4+ human T cells. The internalized RORγt shRNA-CD4 aptamer can be cleaved and released by Dicer and then specifically silenced the targeted RORγt gene expression and results in a marked decrease of Th17 differentiation and IL-17 production. This particular CD4 aptamer does not alter the cell surface levels of CD4 or other activation markers of the host CD4+ T cells. By substituting the shRNA for targeted genes, this CD4 aptamer can be used as a universal vehicle to introduce RNAi into CD4+ T cells. Compared with other vehicles for RNAi delivery into T cells, aptamers have many advantages. First, the size of aptamers is relatively smaller and less likely to be immunogenic. This is particularly critical for in vivo use as therapeutics. Aptamers can be chemically synthesized and it is relatively less expensive to generate aptamer-shRNA/siRNA. Thus, it is of great interest to evaluate the use of this CD4-AshR-RORγt chimera in treatment of Th17 mediated inflammatory disorders.

Example 5

Testing CD4-AsiC-RORC2 in a Hu-SCID Psoriasis Model

A model of psoriasis for use in testing topical pharmaceutical compositions is described in Chang T et al, *Exp Dermatol* 20, 555-560 (2011) which is incorporated by reference herein. Skin biopsy samples of 3-4 cm$^2$ would be obtained from psoriatic lesions of patients with psoriasis and transplanted onto SCID mice at one graft per mouse. Ten days after transplantation, 1×10$^5$ Con A-stimulated PBMC obtained from the same donor that provided the skin sample would be injected intradermally into the xenograft. The clinical and histological features of psoriasis of the xenograft can be maintained for 16-20 weeks.

Other formulations for topical delivery of CD4-AshR-RORγt chimera can include lipid based RNAi delivery media such as GeneCream® provided by TransDerm Inc. This particular composition can be used topically to treat arthritis in a mouse model (Takanashi M et al, *Gene Therapy* 16, 982-989 (2009); incorporated by reference herein). Still other formulations may include DMSO. The formulation used to deliver diclofenac comprises DMSO, propylene glycol, alcohol, glycerin and purified water.

Fifteen and 30 µg doses of CD4-AshR-RORγt formulated for topical administration would be applied to a psoriatic xenograft once every 3 days for a total of 15 days. The xenograft would be harvested for histological, immunohistochemical and immunological analyses.

For histological analysis, samples would be fixed with formalin and embedded in paraffin for sections and histological staining. Thickness of the dermis and dermis can be measured. For immunohistochemical analysis, samples would be snap frozen and cryosections prepared. Staining with anti-IL-17 and anti-CD4 can be performed to identify Th17 cells. Portions of some samples can be digested with collagenase to isolate T cells for flow cytometry. Isolated cells can be stimulated with PMA/ionomycin and intracellular staining for IL-17, IL-22, IL-17F and IFN-γ in com-

The invention claimed is:

1. A recombinant polyribonucleotide comprising a nucleic acid sequence of SEQ ID NO: 1.

2. The recombinant polyribonucleotide of claim 1 wherein the polyribonucleotide is chemically synthesized.

3. The recombinant polyribonucleotide of claim 1 wherein the polyribonucleotide is transcribed from a deoxyribonucleic acid template.

4. The recombinant polyribonucleotide of claim 3 wherein the nucleic acid molecule is transcribed in vitro.

5. The recombinant polyribonucleotide of claim 1 comprising at least one 2'-fluoro ribonucleic acid.

6. The recombinant polyribonucleotide of claim 5 comprising 2'-fluoro cytosine and/or 2'-fluoro uracil.

7. An expression vector comprising:
a first nucleic acid sequence that encodes SEQ ID NO: 1; and
a second nucleic acid sequence comprising a promoter operably linked to the first nucleic acid sequence.

8. The expression vector of claim 7 stably transfected into a cell.

9. A pharmaceutical composition comprising an effective amount of the recombinant polyribonucleotide of claim 1.

10. The pharmaceutical composition of claim 9 formulated for topical administration.

11. A method of treating a disease mediated by Th17 cells in a subject, the method comprising: administering the pharmaceutical composition of claim 9 to the subject, thereby treating the disease mediated by the Th17 cells.

12. The method of claim 11 wherein the disease comprises rheumatoid arthritis, multiple sclerosis, systemic lupus erythematosus, psoriasis, inflammatory bowel disease, and type 1 diabetes mellitus.

* * * * *

SEQUENCE LISTING

```
<160> NUMBER OF SEQ ID NOS: 9

<210> SEQ ID NO 1
<211> LENGTH: 133
<212> TYPE: RNA
<213> ORGANISM: Artificial Sequence
<220> FEATURE:
<223> OTHER INFORMATION: Aptamer-RNAi chimera

<400> SEQUENCE: 1
gggagacaag aauaaacgcu caaugacguc cuuagaauug cgcauuccuc acacaggauc      60
uuuucgacag gaggcucaca acaggccaau cucucuuauc cuugaugugc uuucaaggau     120
aagagagauu guu                                                       133

<210> SEQ ID NO 2
<211> LENGTH: 133
<212> TYPE: RNA
<213> ORGANISM: Artificial Sequence
<220> FEATURE:
<223> OTHER INFORMATION: Aptarmer-RNAi chimera Negative Control

<400> SEQUENCE: 2
gggagacaag aauaaacgcg ucaagaucug ggccuccuua aauaacguac uucguccuaa      60
cuuucgacag gaggcucaca acaggccaau cucucuuauc cuugaugugc uuucaaggau     120
aagagagauu guu                                                       133

<210> SEQ ID NO 3
<211> LENGTH: 133
<212> TYPE: RNA
<213> ORGANISM: Artificial Sequence
<220> FEATURE:
<223> OTHER INFORMATION: Aptamer RNAi Chimera Negative Control

<400> SEQUENCE: 3
gggagacaag aauaaacgcu caaugacguc cuuagaauug cgcauuccuc acacaggauc      60
uuuucgacag gaggcucaca acaggcguuc cuccuaaccu auuuaugugc uuuaaauagg     120
uuaggaggaa cuu                                                       133

<210> SEQ ID NO 4
<211> LENGTH: 135
<212> TYPE: RNA
<213> ORGANISM: Artificial Sequence
<220> FEATURE:
<223> OTHER INFORMATION: Aptamer RNAi Chimera negative control

<400> SEQUENCE: 4
gggagacaag aauaaacgcu caaugacguc cuuagaauug cgcauuccuc acacaggauc      60
uuuucgacag gaggcucaca acaggccucu gcuucggugu cgaaauugug cuuauuucga     120
caccgaagca gaguu                                                     135

<210> SEQ ID NO 5
<211> LENGTH: 86
<212> TYPE: DNA
<213> ORGANISM: Artificial Sequence
<220> FEATURE:
<223> OTHER INFORMATION: Aptamer

<400> SEQUENCE: 5
```

```
gggagacaag aataaacgct caatgacgtc cttagaattg cgcattcctc acacaggatc    60
ttttcgacag gaggctcaca acaggc                                         86

<210> SEQ ID NO 6
<211> LENGTH: 86
<212> TYPE: DNA
<213> ORGANISM: Artificial Sequence
<220> FEATURE:
<223> OTHER INFORMATION: Negative Control Aptamer

<400> SEQUENCE: 6
gggagacaag aataaacgcg tcaagatctg ggcctcctta aataacgtac ttcgtcctaa    60
ctttcgacag gaggctcaca acaggc                                         86

<210> SEQ ID NO 7
<211> LENGTH: 71
<212> TYPE: DNA
<213> ORGANISM: Artificial Sequence
<220> FEATURE:
<223> OTHER INFORMATION: RNAi

<400> SEQUENCE: 7
aacaatctct cttatccttg aaagcacatc aaggataaga gagattggcc tgttgtgagc    60
ctcctgtcga a                                                         71

<210> SEQ ID NO 8
<211> LENGTH: 71
<212> TYPE: DNA
<213> ORGANISM: Artificial Sequence
<220> FEATURE:
<223> OTHER INFORMATION: Negative control RNAi

<400> SEQUENCE: 8
aagttcctcc taacctattt aaagcacata aataggttag gaggaacgcc tgttgtgagc    60
ctcctgtcga a                                                         71

<210> SEQ ID NO 9
<211> LENGTH: 73
<212> TYPE: DNA
<213> ORGANISM: Artificial Sequence
<220> FEATURE:
<223> OTHER INFORMATION: Negative control RNAi

<400> SEQUENCE: 9
aactctgctt cggtgtcgaa ataagcacaa tttcgacacc gaagcagagg cctgttgtga    60
gcctcctgtc gaa                                                       73
```